United States Patent [19]
Corbin et al.

[11] Patent Number: 6,166,258
[45] Date of Patent: *Dec. 26, 2000

[54] PROCESS FOR PREPARING METHYLAMINES USING ACIDIC MOLECULAR SIEVE CATALYSTS

[75] Inventors: David Richard Corbin, West Chester, Pa.; Raul Francisco Lobo, Newark; Stephan Schwarz, Wilmington, both of Del.

[73] Assignee: E. I. du Pont de Nemours and Company, Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 09/409,208

[22] Filed: Sep. 30, 1999

Related U.S. Application Data

[60] Provisional application No. 60/109,975, Nov. 25, 1998.

[51] Int. Cl.[7] .................................................. C07C 209/10
[52] U.S. Cl. ........................................... 564/474; 564/479
[58] Field of Search ...................... 564/474, 479

[56] References Cited

U.S. PATENT DOCUMENTS

| 4,508,837 | 4/1985 | Zones ....................................... 502/62 |
| 4,544,538 | 10/1985 | Zones ....................................... 423/326 |
| 4,683,334 | 7/1987 | Bergna et al. .......................... 564/474 |
| 4,737,592 | 4/1988 | Abrams et al. ......................... 564/479 |
| 4,752,596 | 6/1988 | Bergna et al. ............................ 502/64 |
| 5,194,235 | 3/1993 | Zones ...................................... 423/704 |
| 5,344,989 | 9/1994 | Corbin et al. .......................... 564/479 |
| 5,370,851 | 12/1994 | Wilson .................................... 423/305 |
| 5,399,769 | 3/1995 | Wilhelm et al. ........................ 564/480 |
| 5,569,785 | 10/1996 | Kourtakis et al. ....................... 564/474 |

FOREIGN PATENT DOCUMENTS

| 0 210 718 | 2/1987 | European Pat. Off. ........ C07C 87/08 |
| 0 324 267 | 7/1989 | European Pat. Off. ........ C07C 85/06 |
| 0 893 159 | 1/1999 | European Pat. Off. ......... B01J 29/06 |

OTHER PUBLICATIONS

Wilson, Steve T., Synthesis, Characterization and Sturcture of Sapo–56, A Member of the ABC Double–Six–Ring Family of Materials with Stacking Sequence AABBCCBB, *Microporous and Mesoporous Materials*, 28, 125–137, 1999.

Lobo, Raul F., Synthesis and Rietveld Refinement of the Small–Pore Zeolite SSZ–16, *Chem. Mater.*, 8, 2409–2411, 1996.

*Primary Examiner*—Samuel Barts

[57] ABSTRACT

The present invention relates to the selectivity of production of methylamines from methanol and/or dimethylether and ammonia using at catalytic amount of acidic molecular sieve.

11 Claims, No Drawings

PROCESS FOR PREPARING METHYLAMINES USING ACIDIC MOLECULAR SIEVE CATALYSTS

This application claims priority benefit of U.S. provisional application Ser. No. 60/109,975 filed Nov. 25, 1998, now pending.

FIELD OF THE INVENTION

This invention generally relates to a process for preparation of monomethylamine, dimethylamine and trimethylamine in which methanol and/or dimethylether and ammonia are contacted in the presence of an acidic molecular sieve catalyst with the AFX structure (e.g., SSZ-16). In particular, the reactants are contacted in the presence of an acidic SSZ-16 catalyst, wherein the ratio of silicon to aluminum (Si:Al) in said catalyst is greater than about 2.5:1.

BACKGROUND OF THE INVENTION

Methylamines are generally prepared commercially by continuous reaction of methanol and ammonia in the presence of a dehydration catalyst such as silica-alumina. The reactants are typically combined in the vapor phase, at temperatures in the range of 300° C. to 500° C., and at elevated pressures. Trimethylamine is the principal component of the resulting product stream accompanied by lesser amounts of monomethylamine and dimethylamine. The methylamines are used in processes for pesticides, solvents and water treatment. From a commercial perspective, the most valued product of the reaction is dimethylamine in view of its widespread industrial use as a chemical intermediate (e.g., for the production of dimethylformamide). Thus, a major objective of those seeking to enhance the commercial efficiency of this process has been to improve overall yields of dimethylamine and monomethylamine, relative to trimethylamine. Among the approaches taken to meet this goal are recycling of trimethylamine, adjustment of the ratio of methanol to ammonia reactants and use of selected dehydrating or aminating catalyst species. Many patents and technical contributions are available because of the commercial importance of the process. A summary of some of the relevant art for methylamine synthesis using a variety of catalysts is disclosed in U.S. Pat. No. 5,344,989 (Corbin et al.).

Molecular sieves are important catalysts in the production of methylamines. Molecular sieves have proven useful in catalysis applications because some of them have appreciable acid activity with shape selective features that are not available in the compositionally equivalent amorphous catalyst. Molecular sieves are classified based on their elemental composition and are able to separate components of a mixture based on sizes and shapes of the components. The structure of molecular sieves are based on a three dimensional network of oxygen ions. Within the tetrahedra sites are cations. The $AlO_2^-$ tetrahedra in the structure determine the framework charge which is balanced by cations that occupy non-framework positions.

Molecular sieves that have only $Al^{+3}$ or $Si^{+4}$ cations within their tetrahedra sites are advantageous in methylamine production. These aluminosilicate molecular sieves often are referred to as zeolites. Chabazite and rho zeolites have a common structural framework of eight-member rings of tetrahedral atoms that are often associated with catalytic selectivity for production of dimethylamine from methanol and ammonia. Chabazite zeolites, where the zeolite is derived from mineral sources and the silicon to aluminum ratios in said zeolites is less than about 2:1, as well as rho zeolites are known to be useful as catalysts for methylamines. See U.S. Pat. No. 5,569,785 (Kourtakis et al.) and references cited therein. The catalysts have geometric selectivity which permits the release of dimethylamine and monomethylamine from the zeolite pores. The use of natural H-exchanged and M-exchanged chabazites, where M is one or more alkali metal cations selected from the group consisting of Na, K, Rb and Cs, is disclosed in U.S. Pat. No. 4,737,592 (Abrams et al.).

U.S. Pat. No. 5,399,769 (Wilhelm et al.) discloses an improved methylamines process using synthetic chabazites as catalysts. Runs 3–5 in Table 5 show the methylamines distribution for different synthetic chabazites with a Si:Al ratio of about 2.5:1. The molar ratio of ammonia to methanol was 3.5:1. Such an excess of ammonia is known to decrease trimethylamine formation. The percentage of dimethylamine for each run was 26, 48.7 and 51.5, respectively.

What are needed and are of significant interest to the chemical industry are process improvements which suppress production of trimethylamine and optimize dimethylamine and monomethylamine yields.

SUMMARY OF THE INVENTION

The invention provides a method for the production of dimethylamine (i.e., $(CH_3)_2NH$ or DMA), monomethylamine (i.e., $CH_3NH_2$ or MMA) and trimethylamine (i.e., $(CH_3)_3N$ or TMA), comprising contacting methanol, and/or dimethylether, and ammonia in amounts sufficient to provide a carbon/nitrogen (C:N) ratio from about 0.2 to about 1.5, at a reaction temperature from about 250° C. to about 450° C., in the presence of a catalytic amount of an acidic molecular sieve which has an AFX crystalline structure (e.g., SSZ-16), and wherein the ratio of silicon to aluminum (Si:Al) in said molecular sieve is greater than about 2.5:1, wherein methanol and/or dimethylether is converted to monomethylamine, dimethylamine, and trimethylamine

DETAILED DESCRIPTION OF THE INVENTION

Molecular sieves are well known in the art and are defined in R. Szostak, "Molecular Sieves—Principles of synthesis and Identification," Van Nostrand Reinhold (1989) page 2. The molecular sieves useful for the present invention are those with an AFX structure (e.g., SSZ-16 and SAPO-56). For a description of the AFX structure see R. Lobo et al., Chem. Mater., (1996), 8, pages 2409–2411. The structure of SSZ-16, a synthetic zeolite, is described in this reference. Synthetic SSZ-16 has a composition, as synthesized, and in the anhydrous state in terms of oxide mole ratios of:

(0.5 to 1.4)$R_2O$:(0 to 0.50)$M_2O$:$W_2O_3$ (greater than 5)$YO_2$ where R is an organic cation, M is an alkali metal, W is selected from aluminum, gallium and mixtures thereof and Y is selected from silicon, germanium and mixtures thereof. Further details about the preparation of SSZ-16 can be found in U.S. Pat. Nos. 4,508,837 and 5,194,235, both of which are incorporated herein in their entirety by reference. The alkali metal can be exchanged for H⁺ using mineral acids, by ion exchange or by conversion to an ammoniated form which can then be converted to the acid form by calcination at elevated temperatures, generally ranging from about 400° C. to about 600° C.

Molecular sieves which have the AFX crystal structure, and acidic zeolites wherein the ratio of silicon to aluminum in said zeolites is at least about 2.5:1, preferably greater than about 5:1, can be prepared by heating an aqueous mixture containing an organic nitrogen-containing compound, a silicon oxide source and an aluminum oxide source to a temperature of at least 100° C. The heating is continued until crystals of the desired AFX structure zeolite or riolecular sieve are formed. The preferred organic nitrogen-containing cations for SSZ-16 preparation are described in the two U.S. patents cited immediately above. For SAPO-56 preparation, the preferred organic nitrogen-containing cation is N,N,N', N'-tetramethyl-1,6-hexadiamine.

If desired, the silicon to aluminum ratio of SSZ-16 zeolites can be increased by procedures known in the art such as leaching with chelating agents, e.g., EDTA, or dilute acids.

The process of the present invention comprises contacting methanol and/or dimethylether (DME) and ammonia, in amounts sufficient to provide a carbon:nitrogen (C:N) ratio from about 0.2 to about 1.5, in the presence of a catalytic amount of an acidic molecular sieve, preferably the zeolite SSZ-16, wherein the acidic molecular sieve has a ratio of silicon to aluminum of at least about 2.5:1, preferably 5:1, at a temperature from about 250° C. to about 450° C. Reaction pressures can be varied from about 1 psig–1000 psig (110 kPa–7000 kPa) with a methanol/DME space time of 0.01 hours to 80 hours. The resulting conversion of methanol and/or DME to methylamines is generally in excess of 75% (on a carbon basis) and selectivity (on a carbon basis) to dimethylamine is generally greater than 60%. In addition, selectivity to and yield of trimethylamine is suppressed. Thus, carbon yields of dimethylamine generally exceed 60% and carbon yields of trimethylamine are generally less than 10% under the process conditions of the present invention.

The molar equilibrium conversion of methanol and ammonia to a mixture of the methylamines at 400° C. and a C:N ratio of 1.0 is 17:21:62 (MMA:DMA:TMA).

The variables to be monitored in practicing the process of the present invention include C:N ratio, temperature, pressure, and methanol/DME space time. Space time is calculated as the mass of catalyst divided by the mass flow rate of methanol and DME introduced to a process reactor (mass catalyst/mass methanol+DME fed per hour.)

Generally, if process temperatures are too low, low conversion of reactants to dimethylamine and monomethylamine will result. Increases in process temperatures will ordinarily increase catalytic activity, however, if temperatures are excessively high, equilibrium conversions and catalyst deactivation can occur. Preferably, reaction temperatures are maintained between about 270° C. and about 370° C. more preferably 290° C. to 350° C. with lower temperatures within the ranges essentially preferred in order to minimize catalyst deactivation.

At relatively low pressures, products must be refrigerated to condense them for further purification. Refrigeration adds costs to the overall process. However, excessively high pressures require thick-walled reaction vessels which are also costly. Preferably, pressures are maintained at 10 psig–500 psig (170 kPa–3500 kPa). Short methanol/DME space times result in low conversions and tend to favor the production of monomethylamine.

Long methanol space times may result either in inefficient use of catalyst or production of an equilibrium distribution of the products at very high methanol/DME conversions. Generally, methanol/DME space times of 0.01 hours to 80 hours are satisfactory, with methanol/DME space times of 0.10 hours to 1.5 hours being preferred. These space times correspond to methanol/DME space velocities of 0.013–100 g methanol+DME/g of catalyst/hour, preferably 0.67–10 g of methanol+DME/g of catalyst/hour, respectively.

The molar reactant ratio of methanol and/or dimethylether to ammonia, herein expressed as the C:N ratio (g atoms C/g atoms N), is critical to the process of the present invention. As the C:N ratio is decreased, production of monomethylamine is increased. As the C:N ratio is increased, production of trimethylamine increases. Catalyst deactivation is also greater at high C:N ratios. Accordingly, for best results, C:N ratios should be maintained between 0.2:1 and 1.5: 1, and preferably from 0.5:1 to 1.2:1 in conducting the process of the present invention.

The efficiency of the process of the invention is measured by overall conversion of methanol and/or DME to methylamines, and by selectivity of dimethylamine production. For example, if methanol (MeOH) is used as the sole reactant, overall conversion is determined by comparison of the amount (in moles) of methanol in the product mixture, which is considered to be unconverted, to the amount in the reactant feed. Thus, overall conversion in carbon percent is given by:

$$100(1-(X_{MeOH})/(X_{MeOH}+X_{MMA}+2X_{DMA}+3X_{TMA}+2X_{DME})).$$

Selectivity of methanol to monomethylamine (MMA) in carbon percent, is given by:

$$100(X_{MMA})/(X_{MMA}+2X_{DMA}+3X_{TMA}).$$

Similarly, selectivity of methanol to trimethylamine (TMA), in carbon percent, is given by:

$$100(3X_{TMA})/(X_{MMA}+2X_{DMA}+3X_{TMA}).$$

Selectivity to dimethylamine (DMA) is calculated by analysis of product composition. Thus, selectivity to DMA, in carbon percent, is provided by the following expression:

$$100(2X_{DMA})/(X_{MMA}+2X_{DMA}+3X_{TMA}).$$

Finally, selectivity to dimethylether (DME) in mole percent is given by:

$$100(X_{DME})/(X_{MMA}+X_{DMA}+X_{TMA}+X_{DME});$$

where X in the above equations is the number of moles of the relevant compounds.

For efficient operation, the catalyst must be selective at high conversions (75% to 98%) and a C:N ratio of 0.5:1 to 1.2:1.

In practicing the process of this invention, the molecular sieve catalyst cam be combined with another material resistant to the temperature and other conditions employed in the process. Such matrix materials include synthetic or natural substances such as clays, silicas and metal oxides.

Comparison of selectivities for different samples should be made at similar conversions since selectivity varies with conversion. At low conversions, MMA production is favored, at very high conversions, the reaction will approach an equilibrium distribution and thus result in increased TMA production.

Selectivities can be further improved by modifying the catalyst with a coating, an example of which is described in Bergna et al., U.S. Pat. Nos. 4,683,334 and 4,752,596, the entire contents of which are incorporated by reference herein. Specifically, to improve selectivity, coating of an acidic zeolite which has a SSZ-16 crystalline structure, wherein the ratio of silicon to aluminum (Si:Al) in said zeolite is at least about 5:1 can be accomplished in the following manner: (1) a sample of the catalyst is exposed to the ambient atmosphere and is immersed in tetraethylorthosilicate (TEOS) for 2 hours; (2) the sample is filtered and dried at room temperature overnight; and (3) the sample is then heated in flowing nitrogen at 550° C. for 3 hours. The preceding treatment can be performed with one or more compounds containing at least one element selected from the group consisting of silicon, aluminum, boron and phosphorus, to deposit substantially on the external surfaces of the acidic molecular sieve with the SSZ-16 crystalline structure at least 0.05 weight % of the element.

EXAMPLE 1

Preparation of SSZ-16 and Its Use in the Preparation of Methylamines 1,4-bis(1-azoniabicyclo[2.2.2]octane)butyl dibromide (1.89 g) was dissolved in $H_2O$ (6 mL) and mixed with a sodium silicate solution (5 g, 38.3% solids, $SiO_2/Na_2O$=3.22). The solution was poured into a TEFLON® (polytetrafluoroethylene) lined autoclave followed by the addition of a solution of $Al_2(SO_4)_3 \cdot 18H_2O$ (0.25 g) and NaOH (0.67 g) in $H_2O$ (6 mL). After mixing thoroughly, the autoclave was sealed and the mixture heated, with no stirring, for 6 days at 140° C. under autogeneous pressure. The product was recovered by filtration, then washed with water and dried.

The recovered product was calcined stepwise in a $N_2$/air mixture as follows: brought from room temperature to 93° C. over 2 hours, from 93° C. to 204° C. over 2 hours, from 204° C. to 316° C. over 2 hours, from 316° C. to 427° C. over 2 hours, and from 427° C. to 528° C. over 3 hours. X-ray powder diffraction of this material showed it to be the molecular sieve of the subcategory, zeolite SSZ-16.

This material was ion-exchanged from the $Na^+$ into the $NH_4^+$ form by three exchanges with a 10% $NH_4NO_3$ solution (10 mL/g molecular sieve) at 90° C. for one hour per exchange, and then calcined stepwise again into the $H^+$ form as follows: room temperature to 110° C. at 10° C./minute, 110° C. to 400° C. at 5° C./minute, 400° C. to 450° C. at 1° C./minute and then held at the latter temperature for 8 hours to obtain the catalytically active acidic H-SSZ-16.

Before use in the reactor, the molecular sieve catalyst was pressed into pellets and crushed and sieved to 20 to 40 mesh (0.84 to 0.42 mm). One gram of the resulting catalyst was placed in a stainless steel U-tube reactor, 0.25 in (0.64 mm) in diameter and 18 to 20 inches length (45.7 to 50.8 cm). First, the reactor was heated to reaction temperature in a fluidized sand bath. The reaction pressure was maintained at 200 psig (1480 kPa) to resemble commercial production conditions. Reactants methanol and ammonia were fed to a pre-heater, which consisted of a 2.03 m length by 0.32 mm diameter stainless steel coil at a molar ratio of about 1, vaporized and then passed through the reactor into contact with the catalyst sample. The reactor effluent was continuously measured by gas chromatography for ammonia, dimethylether (DME), methanol, water, and mono-, di- and trimethylamine. The percentage selectivities of conversion to each methylamine species are given in Table 1, below, for conversion of methanol of 79%, which was the maximum conversion obtained.

COMPARATIVE EXAMPLE A

Commercial H-Chabazite

A commercially available sample of H-chabazite (Si:Al= 2.6: 1) obtained from PQ Corporation, Valley Forge, Pa. was used as the methylamines catalyst. The apparatus and procedure were the same as that of Example 1. The percentage selectivities of conversion to each methylamine species are also given for conversion of methanol of 79% in Table 1, below.

COMPARATIVE EXAMPLE B SSZ-13

Zeolite SSZ-13 (Si:Al=12.0:1) was prepared in a similar manner to the method of Zones, U.S. Pat. No. 4,544,538, using N,N,N-trimethyl-1-adamant-ammonium iodide as the organic template (i.e., structure directing agent). The zeolite was calcined at 550° C. to remove the organic template, ion-exchanged with ammonium nitrate to form $NH_4$-H-SSZ-13, and finally calcined at 450° C. in air for 8 hours to obtain the catalytically active acidic H-SSZ-13. The apparatus and procedure were the same as that of Example 1. The percentage selectivities of conversion to each methylamine species are also given in Table 1, below. The conversion of methanol was 79%.

TABLE 1

| Ex. | Reaction Temp. (°C.) | Contact Time[a] | MMA % | DMA % | Combined MMA + DMA | TMA % |
|---|---|---|---|---|---|---|
| 1 | 375 | 67 | 24 | 72 | 96 | 4 |
| A | 300 | 19 | 23 | 59 | 82 | 18 |
| B1 | 350 | 13 | 26 | 70 | 96 | 4 |
| B2* | 350 | 32 | 31 | 68 | 99 | 1 |
| B2** | 350 | 32 | 39 | 59 | 98 | 2 |

[a]Contact time is (minutes)(g catalyst)/(g methanol)
B1 = SSZ-13 sample 1
B2 = SSZ-13 sample 2
(*) and (**) denote reproducibility runs performed with B2

We claim:
1. A method for the production of monomethylamine, dimethylamine, and trimethylamine comprising contacting methanol, and/or dimethylether, and ammonia in amounts sufficient to provide a carbon:nitrogen (C:N) ratio from about 0.2 to about 1.5 and at a reaction temperature from about 250° C. to about 450° C., in the presence of a catalytic amount of an acidic molecular sieve which has an AFX crystalline structure, wherein the ratio of silicon to aluminum (Si:Al) in said molecular sieve is greater than about 2.5:1, wherein methanol and/or dimethylether is converted to monomethylamine, dimethylamine, and trimethylamine.

2. The method of claim 1 wherein the pressure is from 1 kPa to 7000 kPa.

3. The method of claim 1 wherein space time of methanol and/or dimethylether is about 0.01 hours to 80 hours.

4. The method of claim 1 wherein the conversion of methanol and/or dimethylether to monomethylamine, dimethylamine, and trimethylamine is greater than 75%, on a carbon basis.

5. The method of claim 1 wherein the selectivity of conversion, on a carbon basis, to dimethylamine is greater than 60%.

6. The method of claim 1 wherein the selectivity of conversion, on a carbon basis, to trimethylamine is less than 10%.

7. The method of claim 1 wherein the reaction temperature is from about 270° C. to about 370° C. and the reaction pressure is from about 170 kPa–3500 kPa.

8. The method of claim 1 wherein the ratio of silicon to aluminum (Si:Al) in said molecular sieve is about 5.0:1.

9. The method of claim 1 wherein said acidic molecular sieve is SSZ-16.

10. The method of claim 1 wherein said acidic molecular sieve has been modified by treatment with one or more compounds containing at least one element selected from the group consisting of silicon, aluminum, boron and phosphorus, to deposit thereon at least 0.05 weight percent of said element.

11. The method of claim 7 wherein said molecular sieve is SSZ-16.

* * * * *